US009080213B2

United States Patent
Mollenhauer et al.

(10) Patent No.: US 9,080,213 B2
(45) Date of Patent: Jul. 14, 2015

(54) METHODS OF DETERMINING CHONDROCYTES

(75) Inventors: Juergen Mollenhauer, Reutlingen (DE); Christoph Gaissmaier, Kusterdingen-Maehringen (DE)

(73) Assignee: TETEC Tissue Engineering Technologies, Aktiengesellschaft (DE)

( * ) Notice: Subject to any disclaimer, the term of this patent is extended or adjusted under 35 U.S.C. 154(b) by 0 days.

(21) Appl. No.: 13/811,479

(22) PCT Filed: Jul. 27, 2011

(86) PCT No.: PCT/EP2011/062926
§ 371 (c)(1), (2), (4) Date: Feb. 26, 2013

(87) PCT Pub. No.: WO2012/013712
PCT Pub. Date: Feb. 2, 2012

(65) Prior Publication Data
US 2013/0210017 A1 Aug. 15, 2013

(30) Foreign Application Priority Data

Jul. 27, 2010 (DE) .......................... 10 2010 033 565

(51) Int. Cl.
*C12Q 1/68* (2006.01)
*G01N 33/50* (2006.01)
*G01N 33/68* (2006.01)

(52) U.S. Cl.
CPC ............... *C12Q 1/6881* (2013.01); *C12Q 1/68* (2013.01); *G01N 33/5005* (2013.01); *G01N 33/6887* (2013.01); *G01N 2333/4722* (2013.01); *G01N 2333/545* (2013.01); *G01N 2333/71* (2013.01); *G01N 2333/78* (2013.01); *G01N 2333/96494* (2013.01)

(58) Field of Classification Search
CPC ........................................................ C12Q 1/68
USPC ........................................................ 435/6.1
See application file for complete search history.

(56) References Cited

U.S. PATENT DOCUMENTS 5,686,116 A * 11/1997 Bockman et al. ............. 424/650
7,491,392 B2 * 2/2009 Gram et al. ................. 424/139.1
7,795,018 B2 * 9/2010 Kuwana et al. ............... 435/325
8,287,853 B2 * 10/2012 Cool et al. .................... 424/93.1
2009/0098591 A1 4/2009 Richter et al.
2014/0134721 A1 * 5/2014 Thies ............................ 435/347

FOREIGN PATENT DOCUMENTS

DE  10 2006 027 991 A1  12/2007

OTHER PUBLICATIONS

Hoffman, B.E. et al., "Development and Characterization of a Human Articular Cartilage-Derived Chondrocyte Cell Line that Retains Chondrocyte Phenotype," *J. Cell. Physiol.*, 2010, vol. 222, pp. 695-702.

Jeong, C.G. et al., "Three-Dimensional Poly(1,8-octanediol-co-citrate) Scaffold Pore Shape and Permeability Effects on Sub-Cutaneous in vivo Chondrogenesis Using Primary Chondrocytes," *Acta Biomaterialia*, 2011, vol. 7, pp. 505-514.

Shen, Z. et al., "Distribution and Expression of Cartilage Oligomeric Matrix Protein and Bone Sialoprotein Show Marked Changes during Rat Femoral Head Development," *Matrix Biology*, 1994, vol. 14, pp. 773-781.

Goessler, U.R. et al., "In Vitro Analysis of Differential Expression of Collagens, Integrins, and Growth Factors in Cultured Human Chondrocytes," *Otolaryngology-Head and Neck Surgery*, 2006, vol. 134, pp. 510-515.

Elima, K. et al., "Expression of mRNAs for Collagens and Other Matrix Components in Dedifferentiating and Redifferentiating Human Chondrocytes in Culture," *FEB Letters*, Dec. 1989, vol. 258, No. 2, pp. 195-198.

Chu, T-W. et al., "Vascular Endothelial Growth Factor and Its Receptor Expression during the Process of Fracture Healing," *Chinese Journal of Traumatology*, 2008, vol. 11, No. 3, pp. 161-164.

Wu, X. et al., 390 Progression or Initiation of Radiographic Knee Osteoarthritis and the Interleukin-1 Receptor Antagonist Gene, the Johnston County Osteoarthritis Project, *Osteoarthritis and Cartilage*, Oct. 1, 2010, vol. 18, pp. 1063-4584 (1 page of Abstract).

* cited by examiner

*Primary Examiner* — Ardin Marschel
(74) *Attorney, Agent, or Firm* — DLA Piper LLP (US)

(57) ABSTRACT

A method of determining identity, purity and/or potency of chondrocytes in vitro includes a) isolating and, optionally, culturing chondrocytes from a biological sample, and b) determining gene expression of at least one marker in the chondrocytes selected from the group consisting of FLT-1, IL-1beta, BSP-2, and type I collagen.

16 Claims, 2 Drawing Sheets

| Covariate | Graft-Related Adv. Events** | Re-operation (any reason) | Pain | Function | Swelling |
|---|---|---|---|---|---|
| Product Manufacturing and Release Characteristics | | | | | |
| Re-differenciation protocol | 0.61 | 0.74 | 0.91 | 0.52 | 0.26 |
| Cells cryo-preserved | 0.98 | 0.98 | 0.59 | 0.78 | 0.13 |
| Log 10 Celll Number | 0.30 | 0.06 | 0.47 | 0.37 | 0.36 |
| Cell viability at harvest | 0.56 | 0.13 | 0.55 | 0.38 | 0.76 |
| Aggrekan Identity marker 1 dCt | 0.14 | 0.44 | 0.61 | 0.50 | 0.62 |
| BSP-2 Purity marker 1dCt | 0.11 | 0.14 | 0.76 | 0.78 | 0.90 |
| FLT-1 Purity marker 2dCt | *0.02* | *0.03* | 0.21 | 0.67 | 0.81 |
| Kollagen II Positive potency marker 1 dCt | 0.08 | 0.08 | 0.42 | 0.90 | 0.29 |
| Interleukin-1β Negative potency marker 1 dCt | 0.08 | 0.20 | 0.26 | 0.19 | 0.24 |
| Collagen I Negative potency marker 2 dCt | 0.49 | 0.70 | 0.53 | 0.79 | 0.27 |

*P-values derived from the Multivariate Modeling of individual covariates on outcomes of interest in the presence of "time from surgery". **Defined as the subset of adverse events likely related to the graft; "relatedness" was not captured on the survey instrument

Fig. 2

METHODS OF DETERMINING CHONDROCYTES

RELATED APPLICATIONS

This is a §371 of International Application No. PCT/EP2011/062926, with an international filing date of Jul. 27, 2011 (WO 2012/013712 A1, published Feb. 2, 2012), which is based on German Patent Application No. 10 2010 033 565.7, filed Jul. 27, 2010, the subject matter of which is incorporated herein by reference.

TECHNICAL FIELD

This disclosure relates to markers for use in determining pharmaceutical identity, purity and/or potency of chondrocytes, and to methods of determining the pharmaceutical identity, purity and/or potency of chondrocytes, in which methods such markers are determined.

BACKGROUND

Chondrocytes are cells which originate from chondroblasts and are located in cartilage tissue. In fully grown cartilage, chondrocytes lie together in isogenic groups (up to about 10) surrounded by extracellular substance. They make up less than 10% of the bone volume. Owing to their high synthesis activity, they have many organelles and large Golgi complexes. In healthy cartilage, chondrocytes have a low mitosis rate. They synthesize specific matrix components and accumulate them as hyaline cartilage substance, and change their synthesis rate with altered loading pattern.

Hyaline cartilage is found wherever mainly pressure loads occur, which is why it is mostly found in articular cartilage. Nowadays, cartilage defects and degenerative joint diseases are among the most widespread diseases. A distinction is usually made between diseases of the cartilage in which the destruction of articular surfaces can probably be traced back mainly to load impacts, and diseases in which articular degeneration owing to inflammation is at the forefront.

Apart from the (in part very) painful accompanying symptoms of these diseases, they are also a major issue in healthcare since the treatment of joint defects is very cost-intensive which, not least, can also be attributed to the high number of disease cases.

Since the capacity of hyaline cartilage for endogenous regeneration is restricted by nature, a surgical procedure for treating cartilage defects is usually the only alternative for a therapy which is successful to at least some extent. Common to the therapy approaches currently used is the goal of restoring cartilage mass, of a congruent articular surface, of physiological functionality and freedom from pain. Recently, autologous chondrocyte transplantation/implantation (ACT or ACI) in particular has emerged as a preferred measure. In the context of ACT, a cartilage biopsy from a healthy area far from the main articular load zone is removed in a first surgical procedure. From the matrix network of the biopsy, chondrocytes are liberated enzymatically, isolated, and expanded in vitro. After about two weeks and successful cell expansion, the joint is reopened and cleared of debris. Subsequently, a periostal patch (periosteum) from the patient is sutured over the defect, creating a chamber filled with the chondrocyte suspension.

ACT has, however, some disadvantages which have meanwhile been confronted by, in particular, the implantation of cells/chondrocytes applied to biomaterials.

For example, a bioresorbable, biphasic collagen support (NOVOCART® 3D, TETEC AG, Reutlingen, Germany), colonized by autologous chondrocytes, is transplanted into cartilage-bone or pure cartilage defects. While the cells mediate biological restoration of the defective cartilage, the biphasic support facilitates intraoperative handling and provides, in vivo, mechanical protection of the implanted cells and of the newly developing cartilage tissue. Furthermore, the support also ensures that the chondrocytes to be implanted remain at the site of the defect, this being very often quite a big problem in the case of conventional ACT, i.e., ACT with a periostal patch cover.

Nevertheless, the selection, identification and culturing of chondrocytes, both in conventional ACT and in use of support-assisted ACT, or of chondrocyte implantations in general, is a major challenge. This is because chondrocytes can vary greatly with respect to their suitability for use as autologous cells for implantation for cartilage regeneration. This is true not only for chondrocytes from one donor in relation to chondrocytes from another donor, for example, a healthy donor compared to a sick donor, but also for chondrocytes from the same donor. In addition, chondrocytes can change in their properties in an ex vivo culture such that they are no longer as suitable for implantation as when accepted directly after isolation from the donor.

Therefore, it would be desirable to develop a method by which chondrocytes can be checked for their suitability for a prospectively successful chondrocyte transplantation, for example, to have criteria which are indicative thereof.

SUMMARY

We provide a method of determining identity, purity and/or potency of chondrocytes in vitro, including a) isolating and, optionally, culturing chondrocytes from a biological sample, and b) determining gene expression of at least one marker in the chondrocytes selected from the group consisting of FLT-1, IL-1beta, BSP-2, and type I collagen.

BRIEF DESCRIPTION OF THE DRAWINGS

FIG. 2 shows Table 1: an overview of the marker genes and their use as markers in investigating the identity, purity and potency of autologous chondrocytes.

DETAILED DESCRIPTION

Figure 1:
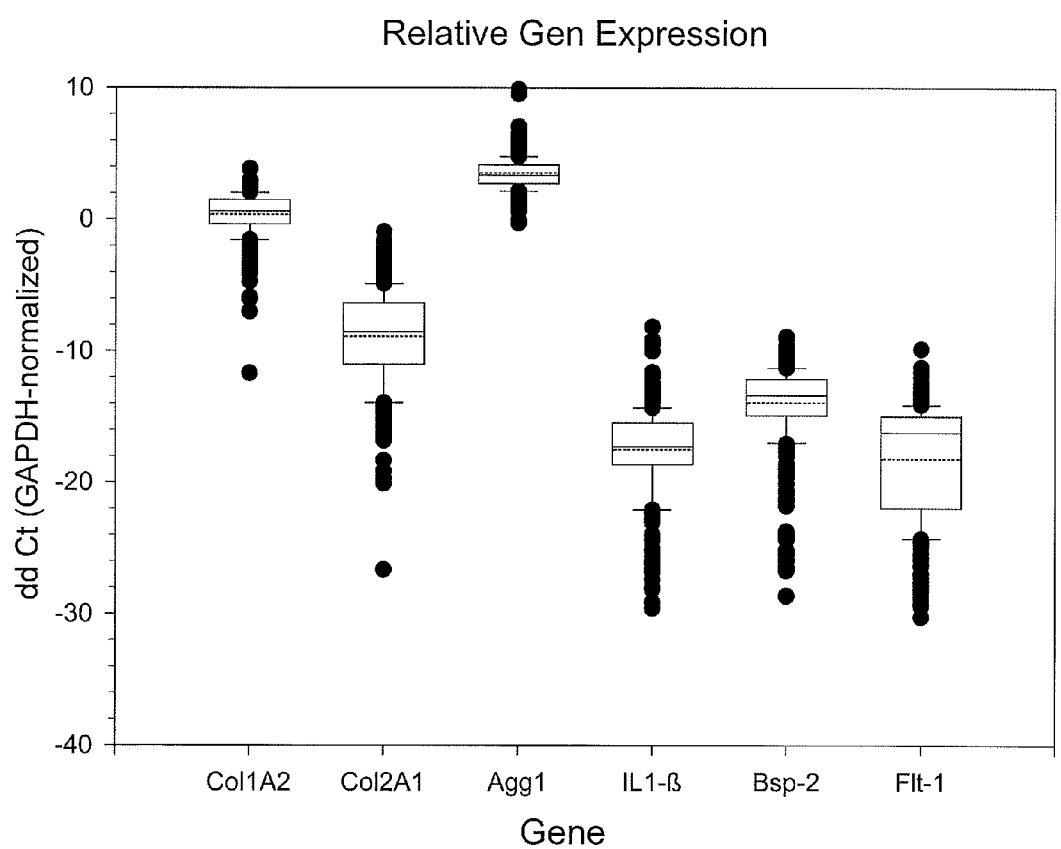
FIG. 1 shows an analysis of relative gene expression of the various marker genes.

We provide for the use of markers or marker genes suitable to determine at least one of the following: viz. identity, purity and potency, and selected from at least one of the following: FLT-1 (receptor for vascular endothelial growth factor), BSP-2 (bone sialoprotein 2), type I collagen, and interleukin (IL)-1beta, wherein expression of the at least one marker is determined.

We further provide a method of determining the identity, purity and/or potency of chondrocytes in vitro, wherein at least one of the following markers is determined in a biological sample comprising chondrocytes: FLT-1, BSP-2, type I collagen, and IL-1beta.

By providing the markers and use thereof, it is possible for the first time to select and to identify, in a targeted manner, chondrocytes which, with respect to their identity, purity and potency, are optimal for a promising chondrocyte transplantation, i.e., represent a chondrocyte population which, first, is sufficiently identified and pure, and which, second, is still active in its ability to reverse the transient proliferative state towards a metabolic state in a stepwise manner.

"Determining" means any genetic and/or biotechnological method by which the marker(s) or expression thereof can be identified in a biological sample, more particularly a chondrocyte-comprising sample.

In addition, "biological sample" means any sample which was taken earlier from a human subject and is assumed to comprise chondrocytes. Preferably, the sample is an articular sample or a cartilage sample, and more preferably a cartilage or articular sample from a site in the body into which an implant for treating cartilage damage is to be inserted, with the chondrocytes present in the biological sample being tested ex vivo directly after collection of the sample and/or else being tested after in vitro culturing.

Our markers offer the possibility not only to select chondrocytes with respect to their anatomical identity, but also especially to confirm chondrocytes with respect to their genetic pattern. In particular, the purity of the chondrocytes thus to be identified is also very important since this ensures that only chondrocytes are purified and ultimately used, rather than also, for example, osteogenic or endothelial cells, which together still have the ability to allow ectopic bone to develop.

In addition, we ensure that use is also made of only chondrocytes which will still, or again, be capable of producing an extracellular matrix, a key property of chondrocytes which is necessary for a successful chondrocyte transplantation.

Accordingly, "potency" means the ability of chondrocytes to resume production of extracellular matrix when the cells are implanted into the defective site to be treated.

Our markers for the first time are therefore an excellent tool which ensures good and sufficient checking of the chondrocytes to be used.

Particular preference is given to determining expression of the marker via the mRNA level, the protein level and/or via a functional test.

Determining the level of the mRNAs and/or of the proteins encoded by the genes is part of the general abilities and knowledge of those skilled in the art. Customary methods include, for example, Northern blot, Western blot, ELISA, and (quantitative) reverse-transcriptase PCR (polymerase chain reaction) techniques.

In particular, preference is given to determining expression of the marker via an elevated mRNA level, an elevated protein level and/or enzymatic activity level. The elevated mRNA level can be determined either as a function of time with regard to a chondrocyte population or else in relation to other cell populations.

In addition, preference is given to the marker being at least one of the following: FLT-1, BSP-2, and type I collagen, and to determining expression thereof via an elevated mRNA level.

This measure has the advantage that an elevated level of the mRNAs of FLT-1, BSP-2, type I collagen makes it possible to clearly determine chondrocytes with respect to their identity, purity (BSP-2 and FLT-1) or potency (type I collagen). Apart from the fact that we found that quantification of type II collagen mRNA and aggrecan mRNA allows a positive statement about the identity of the chondrocytes (the fact of which is to be used in combination with the expression of one or more of the other markers, we also found that quantification of BSP-2 mRNA and of FLT-1 mRNA allows a positive statement about the purity of the chondrocytes or a negative statement about contaminative cell types to be made, since these two markers are typical for subchondral tissues.

"Negative marker" means that when elevated expression is found for one of the genes, the chondrocytes are, for example, not pure (such as for the markers BSP-2 and FLT-1 for example). In contrast, "positive marker" means that elevated expression of these markers confirms the identity of the chondrocytes.

Also, we found that MMP-3 (matrix metalloproteinase 3) or aggrecan, more particularly the 846 epitope, are suitable markers and expression of the marker is determined via an elevated protein level. Advantage may be taken of the fact that a change in the release of the 846 epitope of aggrecan is an indication of a commencing re-differentiation. Hence, an elevated level of this epitope points to a functioning potency. The same applies to MMP-3 since the release of MMP-3 is a positive marker for cartilage regeneration. This finding is used in combination with the expression of one or more of our other markers.

By determining these markers, it is possible to advantageously isolate chondrocytes with respect to the potency thereof to form an extracellular matrix.

Preference may be given to the mRNA of interleukin 1beta (IL-1-beta) being determined, with an elevated IL-1beta mRNA level being used as a negative marker.

As already mentioned further above, we also provide a method of determining the identity, purity and/or potency of chondrocytes in vitro, wherein at least one of the following markers is determined in a biological sample comprising chondrocytes: FLT-1, BSP-2, type I collagen, and IL-1beta. More particularly, our method may have the following steps: a) isolating and, if necessary, culturing chondrocytes from a biological sample, and b) determining gene expression of at least one of the following markers in the chondrocytes: FLT-1, BSP-2, type I collagen, and IL-1beta.

Whilst the identity of chondrocytes can be determined via an elevated gene expression of type II collagen and/or aggrecan, we found that to determine the purity of chondrocytes, an elevated gene expression of FLT-1 and/or BSP-2 can be determined, and to determine the potency of chondrocytes, an elevated gene expression of type I collagen and IL-1beta can be determined.

In our method, in the chondrocytes present in a biological sample, the markers in question are determined with respect to their gene expression, viz. whether they have elevated gene expression for these markers compared to controls and/or over time.

Preference is given to determining elevated gene expression via an elevated mRNA level, an elevated protein level and/or enzymatic activity level.

In particular, preference is given to correlating an elevated mRNA level of type I collagen, type II collagen and/or aggrecan with the identity, purity or potency of chondrocytes, and in particular to inversely correlating an elevated mRNA level of BSP-2 and/or FLT-1 with the purity of chondrocytes, or to correlating an elevated mRNA level of type I collagen, type II collagen with the intact potency of chondrocytes.

Preference may be given to correlating an elevated protein level of aggrecan, more particularly via detection of the 846 epitope, and/or of MMP-3 with the intact potency of chondrocytes.

Analogous to the use, an elevated mRNA level of IL-1beta may be correlated with a lowered potency of chondrocytes.

Overall, preference is given to the markers being used alone or in a combination with one another. The markers can thus each be determined either alone with respect to their gene expression, or else two or more or all can be determined, and the result of the determination of gene expression of the markers can be correlated accordingly with the identity, purity and potency of chondrocytes. In addition, these results can also be further correlated with the mRNA ratio between type I collagen and type II collagen to guarantee correct determination of the chondrocytes.

Therefore, we also provide the markers themselves, viz. for use in determining the identity, purity and/or potency of chondrocytes in a biological sample, wherein the marker is selected from at least one of the following: FLT-1, BSP-2, type I collagen, and IL-1beta.

It will be appreciated that the features mentioned above and to be illustrated below are conceivable not only in the combination specified in each case, but also alone or in other combinations, without departing from the context of this disclosure.

Our methods and markers will be illustrated in more detail below by the figures and the examples.

Example

Characterizing Autologous Chondrocyte Implantation in a Three-Dimensional Matrix (for Example, NOVOCART® 3D) and Identifying Marker Genes During production of three-dimensional matrices loaded with cells for autologous chondrocyte implantation, it is essential to identify the "correct" cells, i.e., chondrocytes to be used for colonization. Characteristics of these cells include (besides viability, cell morphology and proliferative activity) more particularly identity, purity and potency. So that it is possible to investigate these properties in a standardized manner and to determine them with certainty, marker genes have been identified by which these investigations can be carried out.

Besides identification of the marker genes, adverse effects or secondary effects of the implants on the patients were also investigated, and surveys were carried out before and after implantation.

One aim of the investigations was thus also a retrospective view of early results, secondary effects or changes, more particularly with respect to pain, function and swelling in a larger patient group. Furthermore, further analyses were carried out to investigate the effects of the individual patients, of the production and of the product release characteristics on safety and patient results.

For the patients to be investigated who were examined arthroscopically in view of the requirements of treatment with NOVOCART® 3D (TETEC, Reutlingen, see above), two to three cartilage/bone cylinders were removed from the intercondylar notch of the affected joint. After removal of the bone, and of mineralized cartilage, the chondrocytes were isolated mechanically and enzymatically from the remaining cartilage material, and expanded as a primary culture in vitro following good manufacturing practice (GMP).

The NOVOCART® 3D implantation was carried out routinely 21 days after arthroscopy and cell expansion. NOVOCART® 3D was administered with an average cell density of $1.36 \times 10^6$ cells per $cm^2$ defect, with the cells having been applied to the support after they had been harvested from the monolayer culture by trypsinization. For each individual chondrocyte culture batch, viability of the cells was investigated by trypan blue exclusion, and RT-PCR analyses were carried out, wherein six different marker genes were used to investigate the identity, purity and potency of the expanded chondrocytes.

These marker genes were selected on the basis of previous in vitro and in vivo experiments using human articular chondrocytes to investigate their ability to form cartilage and to assess the respective articular environment for cartilage replacement.

Both the respective surgeons of the patients and the patients themselves completed appropriate data sheets, with the patients not only providing fundamental demographic data, but also giving details with regard to self-assessment of the surgical results such as, for example, with respect to the degree of pain and functionality.

The rating of the surgical results and the adverse effects were collected and statistically recorded. The survey was carried out in all the clinical centers in Germany in which 433 patients implanted with NOVOCART® 3D were treated. Overall, data for 422 patients were recorded, of which 140 were female and 282 were male. The average age was 33.4 years.

Statistics, including mean values, standard deviations, confidence intervals, were used to present summaries of the adverse effects, of the efficiency of the operations, and to present patient characteristics. Chi-square tests and regression models were constructed to investigate associations between production or release characteristics and the five surgical result ratings of the patient surveys: implant-based adverse effects (defined as the summarizing collection of implant failure, delamination, hypertrophy, arthrofibrosis, adhesion, chondromalacia, joint infection and the presence of osteochondral fragments (detached cartilage-bone fragments)), repeat operation (for whatever reason), and changes with respect to the baseline of pain, function, and degree of swelling of the affected joint.

To investigate the cellular and biomolecular characteristics, the viability of chondrocytes was investigated during removal (% living cells), as were the mRNA expression levels of six different marker genes in the chondrocytes, viz. FLT-1, BSP-2, type I collagen/type II collagen, aggrecan, interleukin 1beta and MMP-3, with respect to the identity, purity and potency of chondrocytes.

For this purpose, the mRNA of the individual markers was assessed in each case by qRT-PCR (quantitative reverse-transcriptase polymerase chain reaction). Expression of glyceroldehyde 3-phosphate dehydrogenase (GAPDH) was used for normalization of the values determined. After ex vivo expansion of the chondrocytes, the mRNA was isolated from the cells and investigated with respect to the particular markers. We found that increased expression of type II collagen combined with increased expression of aggrecan is an excellent marker, or an excellent marker combination, providing proof of a suitable chondrocyte cell line. In addition, the markers FLT-1 and BSP-2 were identified as negative markers, i.e., increased expression of these two genes indicates impure chondrocyte populations. The threshold value indicating an impure population was less than 50 mRNA copies per 1000 cells (<0.001/GAPDH). With respect to the chondrocyte potency to be investigated, the marker genes type I collagen/type II collagen, or their ratio, were identified as a suitable marker/marker combination, and to determine the type I collagen/type II collagen ratio on day 19 after ex vivo expansion, the cells were harvested and the marker genes, as explained above, were investigated by qRT-PCR and related to one another. It is also possible to determine potency by determining expression of IL-1beta, with an increased IL-1beta value being a negative marker and this fact, for example, also in combination with the value for the type I collagen/type II collagen ratio, can be used to determine potency.

Aggrecan (846 epitope) and MMP-3 were identified as further markers which can be used for potency. Both proteins were detected by ELISA, on days 4, 19 and 20. Quantitative protein expression of the 846 epitope and of MMP-3, or their elevated level, are important indicators for a functional potency of chondrocytes.

FIG. 1 shows the analysis of gene expression when the chondrocytes were harvested from expanded monolayer cultures. The data were obtained from PCR experiments according to standard protocols as described above, before the cells were seeded on the biphasic support material.

In some cases, comparative biopsies were taken of patients who had received conventional ACI or were subjected to the NOVOCART® 3D method. These biopsies were collected in physiological saline, briefly fixed in buffered 4% paraformaldehyde and embedded in a frozen-section carrier (TissueTek), and kept at −20° C. until production of the sections. In each case, 10 sections were produced, and stained with haematoxylin eosin (HE) or Safranin O—Fast Green (SafO), or immunostained with primary monoclonal antibodies to type I and type II collagens, aggrecan (anti-type I collagen; 1 mg/ml (monoclonal mouse; species specificity: human; MP Biomedical*63170 I-8H5); anti-type II collagen; 1 mg/ml (monoclonal mouse; species specificity: broad; developmental studies Thomas F. Linsenmeyer*II-II6B3); anti-aggrecan; 0.75 mg/ml (monoclonal mouse; species specificity: human/bovine; Acris*SM1353)). Detection was carried out with fluorescent secondary antibodies (Cy3-conjugated AffiniPure goat, anti-mouse IgG+M; 0.75 mg/ml; (Jackson, Dianova; #115-165-044)).

Prior to the surgical procedure, the respective surgeons examined the patient and rated the examinations with respect to joint pain, function and swelling on a scale of 1 to 10, where higher values indicated a better surgical result. Patients for whom the survey results were evaluated pre-operatively and post-operatively exhibited significant improvements over the baseline (p<0.0001, Wilcoxon signed-rank test).

With respect to the occurrence of adverse effects, the following was found: implant failure occurred in 3.1% of the total patient population. Overall, the reported rates for implant-based complications for the total patient population were very low. Delamination, arthrofibrosis and hypertrophy were observed at 1.7%, 2.4% and 0.7%, respectively.

A total of 36 patients (8.5%) required a repeat operation and/or revision. The most common adverse affects for patients who required a repeat operation were implant failure (13), delamination (6), arthrofibrosis (7), synovitis (7), adhesion (5) and pain (6).

The size of all the treated defects did not correlate with the adverse affects. However, the change in the baseline for the function was significantly associated with the age of the patients, meaning that the younger patients showed on average greater improvements, p=0.004 (data not shown).

In addition, implant-based adverse effects and repeat operations were mostly independent of the location of the primary defect, with the exception of patella defects.

Assessment of the association between the classification of the cartilage defect and the occurrence of implant-based adverse effects revealed that a patient was more likely to report adverse effects when the cartilage defect was assessed to be degenerative (p=0.005). In the case of patients with a cartilage defect caused by osteochondrosis dissecans, fewer of such adverse effects were reported (p=0.04).

During the retrospective and prospective clinical evaluations with NOVOCART® 3D, the stored cDNAs of the patients were analysed to determine simultaneously the gene expression levels of the markers type I collagen (Col1), type II collagen (Col2), aggrecan (Agg), interleukin 1beta (IL-1b), bone sialoprotein 2 (BSP-2) and the endothelial VEGF receptor FLT-1. These data sets were then combined with the clinical operative results, and associations between the production processes and implant release characteristics, and clinical results were investigated.

The additional use of the re-differentiation protocol for seeded chondrocytes in the biphasic support or temporary cryopreservation of the cells was not associated with a greater occurrence of implant-based adverse effects or with significant differences in other surgical results. The same results were observed for the cell numbers administered.

The results of these investigations are shown in FIG. 2 (Table 1).

In the table in FIG. 2, a significant association can be seen between implant-based adverse effects and the expression levels of the marker genes. For instance, an elevated expression level for one of the chosen markers for molecular contamination of chondrocytes (FLT-1) was associated with implant-based adverse effects (p=0.02). Threshold values were found with respect to an elevated expression level of a marker (type I collagen) for negative potency, as was a reduced expression level of a positive potency marker (type II collagen) (see also FIG. 2=Table 1), showing that these potency markers are also suitable to check the potency, purity and identity of the chondrocytes which are to be used in each case and which are used with the biphasic support or generally in ACI. In contrast, an association between the disappearance of pain and elevated coexpression of the identity marker and of the positive potency marker (type II collagen) for chondrocytes was found.

In summary, the identified markers for identity, purity and potency are suitable to confirm the chondrogenic phenotype of the expanded cells. With the markers, it was possible to show that the method used for producing NOVOCART® 3D supports is safe and that the cell number administered is within the window for therapeutic efficiency. The markers were used as follows:

Type I collagen and interleukin 1beta: negative potency markers; type II collagen: positive potency marker; FLT-1, BSP-2: negative purity markers; aggrecan: positive identity marker.

Furthermore, threshold biases for implant-based secondary effects were identified, and it was possible to trace these back both to increased expression of the negative potency marker (type I collagen) and to increased expression of the positive potency marker. The positive potency marker is associated with the chondrogenic degree of differentiation of the expanded chondrocytes, whereas the negative potency marker is associated with local joint inflammation, and also with apoptosis (controlled cell death) and a more catabolic metabolism of the chondrocytes. However, increased co-expression levels of the identity and positive potency markers were accompanied by a decline or disappearance of pain after implantation of the NOVOCART® 3D.

Overall, these data suggest that both the quality of the implanted chondrocytes and the molecular environment of the particular joint can influence the clinical result. Using the novel markers, it is therefore possible to predict not only the actual quality of the cells and of the implant but also, in part, clinical success.

The invention claimed is:

1. A method of determining identity, purity and/or potency of chondrocytes in vitro, comprising:
   a) isolating and, optionally, culturing chondrocytes from a biological sample, and
   b) determining gene expression of at least one marker in the chondrocytes selected from the group consisting of FLT-1, IL-1beta, BSP-2, and type I collagen, type II collagen, and aggrecan, wherein identity of the chondrocytes is determined via an elevated gene expression of type II collagen and/or aggrecan, purity of the chondrocytes is determined by determining gene expression of FLT-1 and BSP-2, and increased gene expression of these genes is used as a negative marker for the purity of the chondrocytes, and potency of the chondrocytes is determined by determining gene expression of type 1 collagen and IL-1 beta, and the increased gene expression of these genes is used as a negative marker for the potency of the chondrocytes.

2. The method according to claim 1, wherein the potency of chondrocytes is further determined by determining gene expression of the type I collagen/type II collagen ratio.

3. The method according to claim 1, wherein an elevated mRNA level of FLT-1, type I collagen, and BSP-2, is further correlated with the identity, purity or potency of chondrocytes.

4. The method according to claim 3, wherein an elevated mRNA level of FLT-1 and/or BSP-2 further inversely correlates with the purity of chondrocytes.

5. The method according to claim 2, wherein an elevated mRNA level of a type I collagen/type II collagen ratio further correlates with the intact potency of chondrocytes.

6. The method according to claim 2, wherein an elevated mRNA level of IL-1beta is further correlated with a lowered potency of chondrocytes.

7. The method according to claim 5, wherein the gene expression of at least two markers is determined.

8. The method according to claim 7, wherein the markers are used in further combination with the markers type II collagen, aggrecan and/or MMP-3.

9. The method according to claim 8, wherein the expression of the markers type II collagen, aggrecan and/or MMP-3 is determined via the mRNA level.

10. The method according to claim 3, wherein an elevated mRNA level of a type I collagen/type II collagen ratio further correlates with the intact potency of chondrocytes.

11. The method according to claim 2, wherein the gene expression of at least two markers is determined.

12. The method according to claim 3, wherein the gene expression of at least two markers is determined.

13. The method according to claim 4, wherein the gene expression of at least two markers is determined.

14. The method according to claim 5, wherein the gene expression of at least two markers is determined.

15. The method according to claim 6, wherein the gene expression of at least two markers is determined.

16. A method of determining purity and/or potency of chondrocytes in vitro, comprising:
   a) isolating and, optionally, culturing chondrocytes from a biological sample, and
   b) determining gene expression of at least one marker in the chondrocytes selected from the group consisting of FLT-1, IL-1 beta, BSP-2, and type I collagen, wherein the purity of the chondrocytes is determined by determining gene expression of FLT-1, and BSP-2, and increased gene expression of these genes is used as a negative marker for purity of chondrocytes, and potency of the chondrocytes is determined by determining gene expression of type I collagen and IL-1 beta, and increased gene expression of these genes is used as a negative marker for the potency of the chondrocytes.

* * * * *